United States Patent
Schirmer

(10) Patent No.: US 10,344,004 B2
(45) Date of Patent: Jul. 9, 2019

(54) INHIBITOR OF THE MUTATED ISOCITRATE DEHYDROGENASE IDH1 R132H

(71) Applicant: Bayer Pharma Aktiengesellschaft, Berlin (DE)

(72) Inventor: Heiko Schirmer, Solingen (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 15/748,014

(22) PCT Filed: Jul. 22, 2016

(86) PCT No.: PCT/EP2016/067477
§ 371 (c)(1),
(2) Date: Jan. 26, 2018

(87) PCT Pub. No.: WO2017/016992
PCT Pub. Date: Feb. 2, 2017

(65) Prior Publication Data
US 2018/0222870 A1    Aug. 9, 2018

(30) Foreign Application Priority Data
Jul. 27, 2015 (EP) ..................................... 15178419

(51) Int. Cl.
*C07D 235/30* (2006.01)
*A61P 35/00* (2006.01)

(52) U.S. Cl.
CPC ............ *C07D 235/30* (2013.01); *A61P 35/00* (2018.01)

(58) Field of Classification Search
CPC ................................................... C07D 235/30
See application file for complete search history.

(56) References Cited

U.S. PATENT DOCUMENTS

| | | | | |
|---|---|---|---|---|
| 9,951,027 | B2 * | 4/2018 | Rehwinkel | C07D 235/30 |
| 9,957,235 | B2 * | 5/2018 | Rehwinkel | C07D 235/30 |
| 10,138,226 | B2 | 11/2018 | Rehwinkel et al. | |
| 2017/0319549 | A1 * | 11/2017 | Rehwinkel | C07D 401/04 |
| 2017/0320861 | A1 * | 11/2017 | Rehwinkel | C07D 409/12 |
| 2018/0170882 | A1 * | 6/2018 | Ring | C07D 235/24 |
| 2018/0201585 | A1 * | 7/2018 | Panknin | C07D 235/30 |
| 2018/0207137 | A1 | 7/2018 | Panknin et al. | |
| 2018/0215717 | A1 * | 8/2018 | Panknin | C07D 235/30 |
| 2018/0222871 | A1 * | 8/2018 | Schirmer | A61P 35/00 |

FOREIGN PATENT DOCUMENTS

| | | | |
|---|---|---|---|
| WO | WO2010151441 A1 | 12/2010 | |
| WO | WO2013046136 A1 | 4/2013 | |
| WO | WO2015121209 A1 | 8/2015 | |
| WO | WO-2015121210 A1 * | 8/2015 | C07D 235/30 |
| WO | WO2015121210 A1 | 8/2015 | |
| WO | WO2016062677 A1 | 4/2016 | |
| WO | WO2016062770 A1 | 4/2016 | |
| WO | WO2016198322 A1 | 12/2016 | |
| WO | WO2017005674 A1 | 1/2017 | |
| WO | WO2017009325 A1 | 1/2017 | |
| WO | WO2017012967 A1 | 1/2017 | |
| WO | WO2017017046 A1 | 2/2017 | |

OTHER PUBLICATIONS

J. Shi et al., 221 Annals of Operations Research, 331-356 (2014).*
Z. Wang et al., 19 Drug Discovery Today, 145-150 (2014).*
U.K. Marelli et al., 3 Frontiers in Oncology, 1-12 (2013).*
S. Jones et al., 59 Journal of Medicinal Chemistry, 11120-11137 (2016).*
E. Pelosi et al., 1 Journal of Exploratory Research in Pharmacology, 20-34 (2016).*
Balss, J. et al. (2012) "Enzymatic assay for quantitative analysis of (D)-2-hydroxyglutarate," Acta Neuropathol; 124:883-891.
French, C. et al. (2012) "Pathogenesis of NUT Midline Carcinoma," Annu. Rev. Pathol. Mech. Dis. 7:247-65.
International Search Report and Written Opinion dated Oct. 11, 2016 for International Application No. PCT/EP2016/067477 filed Jul. 22, 2016, 8 pages.
Mohrenz, I. et al. (2013) "Isocitrate dehydrogenase 1 mutant R132H sensitizes glioma cells to BCNU-induced oxidative stress and cell death," Apoptosis, 18:1416-1425.
Prensner, J. et al. (Mar. 2011) "Metabolism unhinged: IDH mutations in cancer," Nature Medicine, 12(3):291-293.
Rosman, K. et al. (1998) "Isotopic Compositions of the Elements 1997," Pure & Appl. Chem., 70(1):217-235.
U.S. Appl. No. 15/520,384, filed Apr. 19, 2017, for Hartmut Rehwinkel et al. (A copy of U.S. Patent Application is not submitted herewith pursuant to the waiver of 37 C.F.R § 1.98(a)(2)(iii) issued by the Office on Sep. 21, 2004.) (Also published as US-20170319549, cited herewith).
U.S. Appl. No. 15/580,372, filed Dec. 7, 2017, for Sven Ring et al. (A copy of U.S. Patent Application is not submitted herewith pursuant to the waiver of 37 C.F.R § 1.98(a)(2)(iii) issued by the Office on Sep. 21, 2004.) (Also published as US-20180170882, cited herewith).
U.S. Appl. No. 15/742,363, filed Jan. 5, 2018, for Olaf Panknin et al. (A copy of U.S. Patent Application is not submitted herewith pursuant to the waiver of 37 C.F.R § 1.98(a)(2)(iii) issued by the Office on Sep. 21, 2004.) (Also published as US-20180207137, cited herewith).

(Continued)

*Primary Examiner* — Alexander R Pagano

(74) *Attorney, Agent, or Firm* — Morrison & Foerster LLP

(57) ABSTRACT

The present invention relates to the adduct (2E)-but-2-enedioic acid-3-(2-{[4-(trifluoromethoxy)phenyl]amino}-1-[(1R,5R)-3,3,5-trimethylcyclohexyl]-1H-benzimidazol-yl)propanoic acid (1:4), methods for preparing this adduct, pharmaceutical compositions comprising this adduct and also the use of this adduct for preparing a medicament for the treatment of a disease.

11 Claims, 5 Drawing Sheets

(56) References Cited

OTHER PUBLICATIONS

Figure 1A:
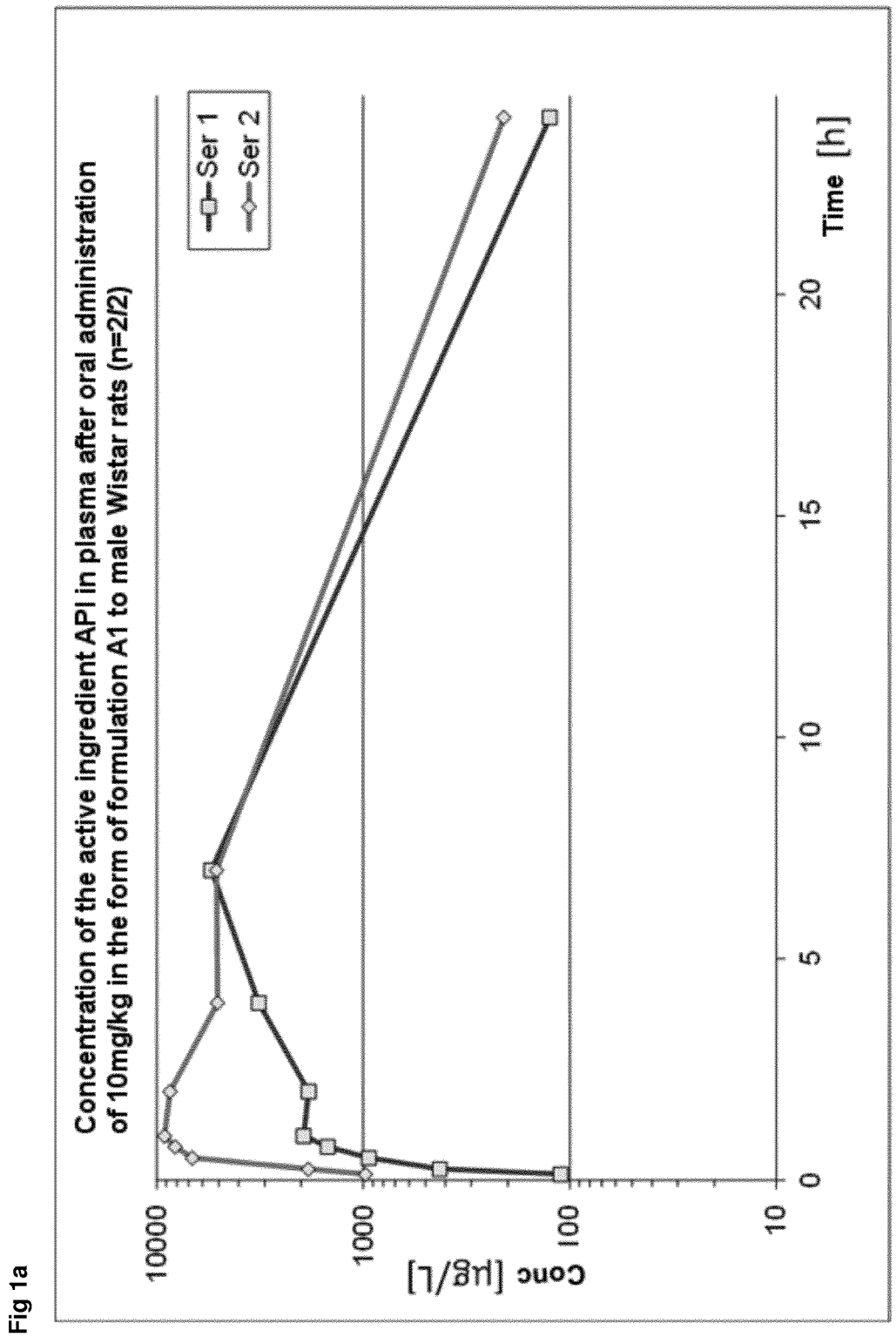

U.S. Appl. No. 15/744,641, filed Jan. 12, 2018, for Olaf Panknin et al. (A copy of U.S. Patent Application is not submitted herewith pursuant to the waiver of 37 C.F.R § 1.98(a)(2)(iii) issued by the Office on Sep. 21, 2004.) (Also published as US-20180201585, cited herewith).

U.S. Appl. No. 15/746,352, filed Jan. 19, 2018, for Olaf Panknin et al. (A copy of U.S. Patent Application is not submitted herewith pursuant to the waiver of 37 C.F.R § 1.98(a)(2)(iii) issued by the Office on Sep. 21, 2004.) (Also published as US-20180215717, cited herewith).

U.S. Appl. No. 15/748,027, filed Jan. 26, 2018, for Heiko Schirmer et al. (A copy of U.S. Patent Application is not submitted herewith pursuant to the waiver of 37 C.F.R § 1.98(a)(2)(iii) issued by the Office on Sep. 21, 2004.) (Also published as US-20180222871, cited herewith).

U.S. Appl. No. 15/923,895, filed Mar. 16, 2018, for Hartmut Rehwinkel et al. (A copy of U.S. Patent Application is not submitted herewith pursuant to the waiver of 37 C.F.R § 1.98(a)(2)(iii) issued by the Office on Sep. 21, 2004.).

* cited by examiner

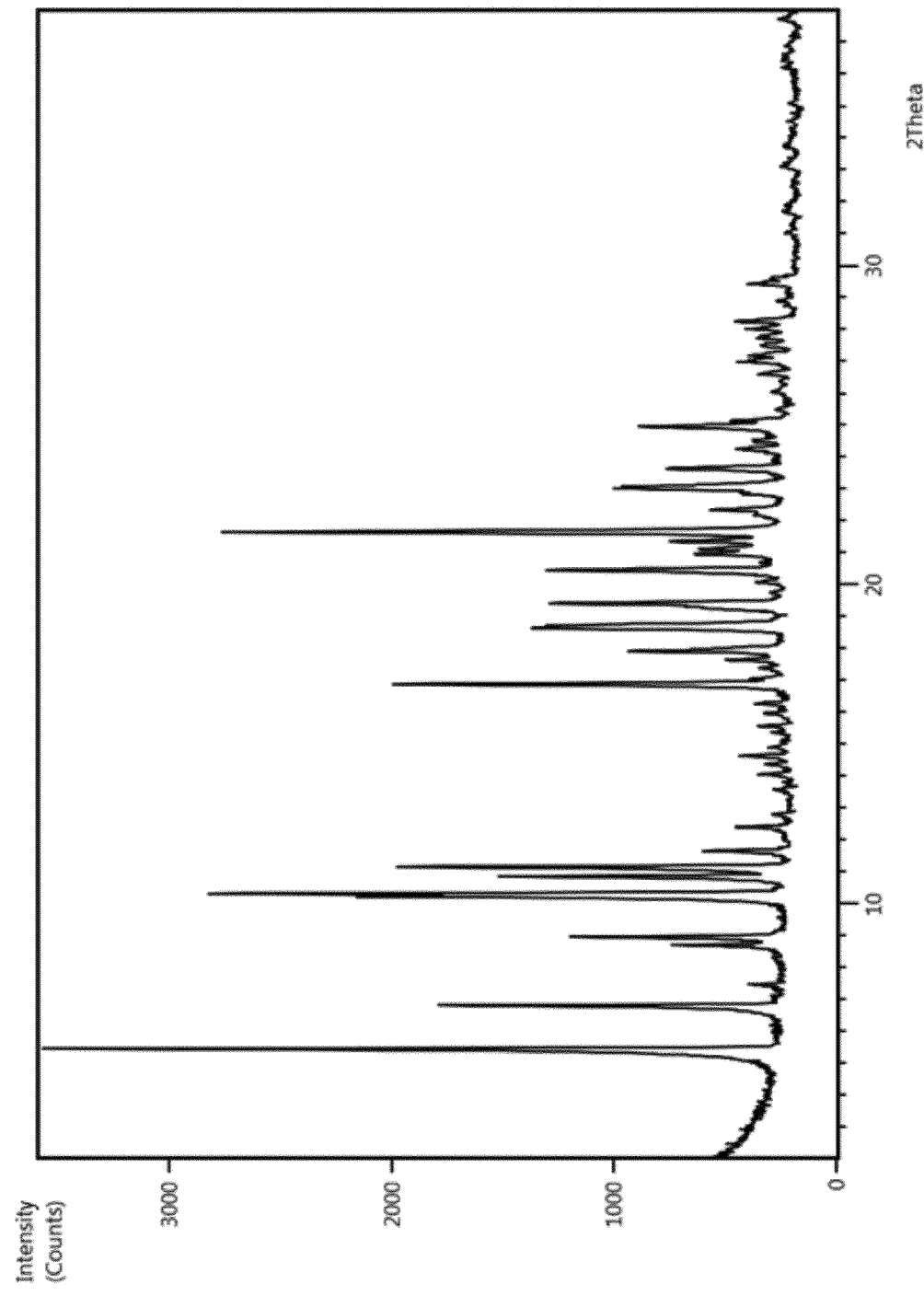
Fig. 2: X-ray diffractogram

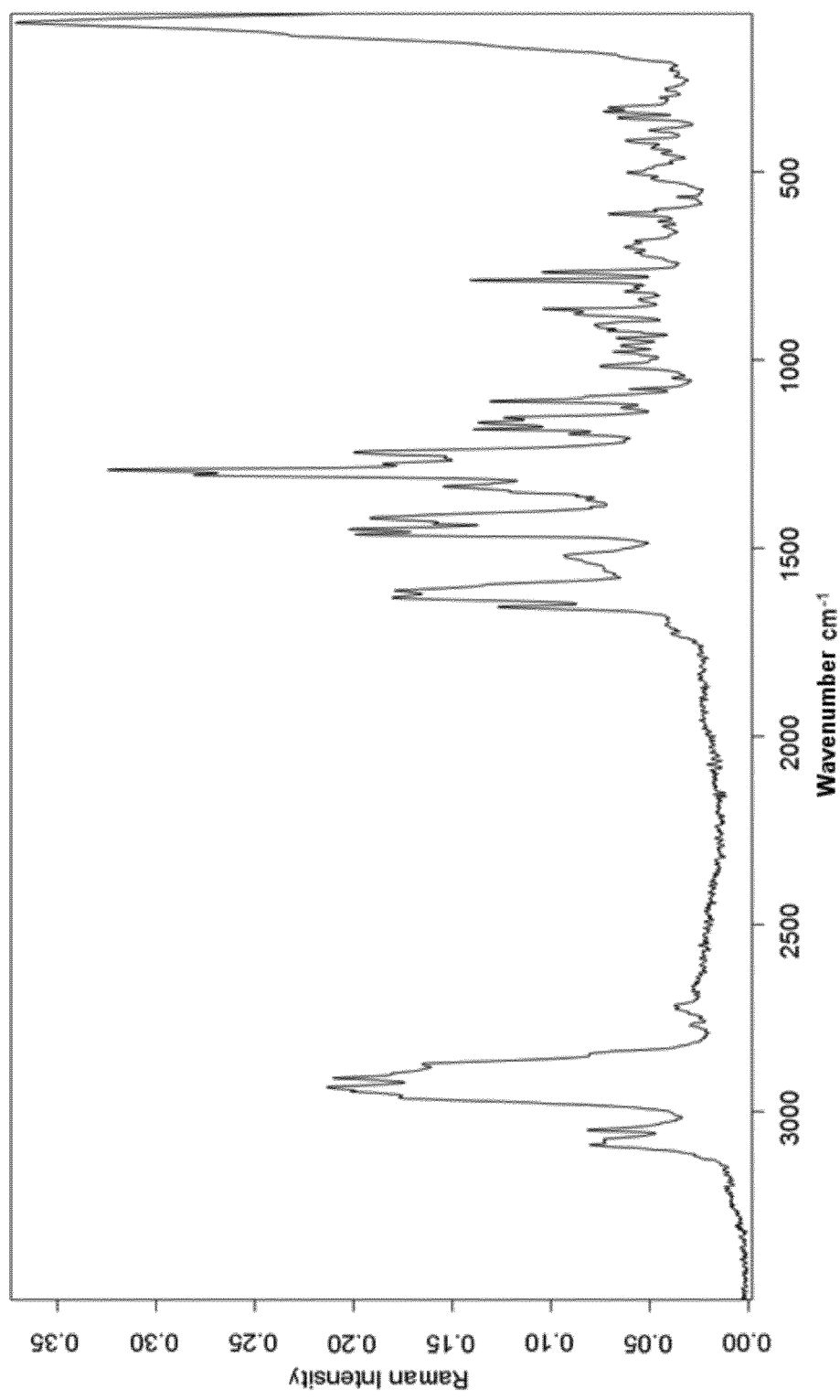
Fig. 3: Raman spectrum

INHIBITOR OF THE MUTATED ISOCITRATE DEHYDROGENASE IDH1 R132H

CROSS REFERENCE TO RELATED APPLICATIONS

This application is a National Phase application under 35 U.S.C. § 371 of International Application No. PCT/EP2016/067477, filed Jul. 22, 2016, which claims priority benefit of European Application No. 15178419.6, filed Jul. 27, 2015.

The present invention relates to the adduct (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4), methods for preparing this adduct, pharmaceutical compositions comprising this adduct and also the use of this adduct for preparing a medicament for the treatment of a disease.

INTRODUCTION 3-(2-Anilino-1-cyclohexyl-1H-benzimidazol-5-yl)propanoic acid is disclosed in the published specification WO2015/121210(A1) as an inhibitor of the mutated isocitrate dehydrogenase IDH1 R132H.

IDH1 R132H is involved in various cellular processes such as the citrate cycle, lipid metabolism, repair processes such as histone methylation and DNA methylation (Prensner, J. R., and Chinnaiyan, A. M.: Metabolism unhinged: IDH mutations in cancer, Nature Medicine 2011, 17, 291-293). The inhibition of the IDH1 mutation represents a promising therapy in the treatment of tumours.

Based on the prior art, the object consisted of providing highly potent inhibitors of the mutated isocitrate dehydrogenase IDH1 R132H, which may be used for the treatment of a disease of the human and/or animal body, in particular for the treatment of tumours.

DESCRIPTION OF THE INVENTION

The present invention relates to (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4), also referred to below as adduct or adduct according to the invention.

This takes the form of an adduct comprising one molecule of fumaric acid to four molecules of 3-(2-{[4-(trifluoromethoxy)phenyl]amino}-1-[(1R,5R)-3,3,5-trimethylcyclohexyl]-1H-benzimidazol-5-yl)propanoic acid.

The structural formula of the individual constituents are shown below: 3-(2-{[4-(trifluoromethoxy)phenyl]amino}-1-[(1R,5R)-3,3,5-trimethylcyclohexyl]-1H-benzimidazol-5-yl)propanoic acid

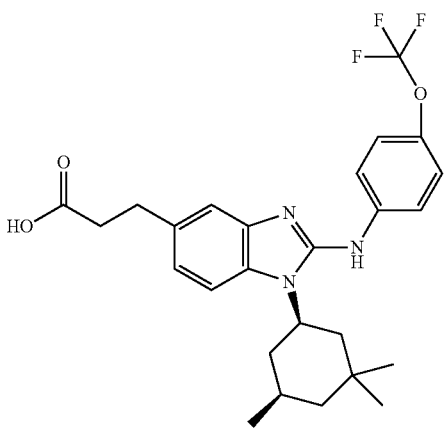 [SMILES: C[C@H]1C[C@@H](n2c(Nc3ccc(OC(F)(F)F)cc3)nc3cc(CCC(=O)O)ccc32)CC(C)(C)C1]

(2E)-but-2-enedioic acid (fumaric acid)

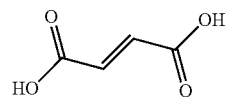

It has been found, surprisingly, that this adduct has a higher bioavailability compared to the free 3-(2-{[4-(trifluoromethoxy)phenyl]amino}-1-[(1R,5R)-3,3,5-trimethylcyclohexyl]-1H-benzimidazol-5-yl)propanoic acid.

In the meantime, investigations by X-ray crystallography have been able to show that the adduct is a salt, i.e. it results from transfer of protons from the fumaric acid to the 3-(2-anilino-1-cyclohexyl-1H-benzimidazol-5-yl)propanoic acid.

The adduct is preferably present in crystalline form.

The present invention also relates to a crystalline form of (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4), which is characterized by maxima in the X-ray diffractogram at the following 2 theta angles: 5.4, 6.8, 10.2, 10.3, 10.8, 11.1, 16.8, 21.6.

The present invention also relates to a crystalline form of (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4), which is characterized by maxima in the Raman spectrum at the following wavenumbers (the values are in units of $cm^{-1}$):

3088, 3047, 2934, 2910, 2874, 2771, 2717, 1658, 1632, 1615, 1521, 1463, 1451, 1420, 1338, 1306, 1294, 1277, 1245, 1198, 1184, 1167, 1155, 1127, 1109, 1077, 1049, 1018, 979, 961, 943, 922, 908, 877, 866, 839, 817, 789, 767, 714, 700, 685, 646, 631, 613, 568, 517, 503, 450, 438, 416, 388, 358, 339, 330, 102.

The adduct according to the invention may be prepared by dissolving 3-(2-{[4-(trifluoromethoxy)phenyl]amino}-1-[(1R,5R)-3,3,5-trimethylcyclohexyl]-1H-benzimidazol-5-yl)propanoic acid in isopropanol with an excess (based on the molar ratio of the constituents of the adduct) of (2E)-but-2-enedioic acid. Preference is given to a molar ratio of 0.3 to 0.8 parts (2E)-but-2-enedioic acid relative to 1 part 3-(2-{[4-(trifluoromethoxy)phenyl]amino}-1-[(1R,5R)-3,3,5-trimethylcyclohexyl]-1H-benzimidazol-5-yl)propanoic acid, particular preference being given to using 0.5 parts (2E)-but-2-enedioic acid relative to 1 part 3-(2-{[4-(trifluoromethoxy)phenyl]amino}-1-[(1R,5R)-3,3,5-trimethylcyclohexyl]-1H-benzimidazol-5-yl)propanoic acid.

On distilling off the isopropanol, the adduct crystallizes out and may be isolated.

The present invention further provides a method for preparing the adduct according to the invention.

The method comprises the steps of
introducing 3-(2-{[4-(trifluoromethoxy)phenyl]amino}-1-[(1R,5R)-3,3,5-trimethylcyclohexyl]-1H-benzimidazol-5-yl)propanoic acid and (2E)-but-2-enedioic acid in isopropanol, wherein for 1 mol of 3-(2-{[4-(trifluoromethoxy)phenyl]amino}-1-[(1R,5R)-3,3,5-trimethylcyclohexyl]-1H-benzimidazol-5-yl)propanoic acid, 0.3 to 0.8 mol of (2E)-but-2-enedioic acid are used,
heating the mixture with stirring up to the boiling point to obtain a clear solution,
crystallizing out of (2E)-but-2-enedioic acid 3-(2-{[4-(trifluoromethoxy)phenyl]amino}-1-[(1R,5R)-3,3,5-trimethylcyclohexyl]-1H-benzimidazol-5-yl)propanoic acid (1:4), preferably by concentrating the solution.

3-(2-{[4-(Trifluoromethoxy)phenyl]amino}-1-[(1R,5R)-3,3,5-trimethylcyclohexyl]-1H-benzimidazol-5-yl)propanoic acid can be prepared analogously to the method disclosed in WO2010/151441 for 4-(1-cyclopentyl-1H-benzo[d]imidazol-2-ylamino)-N-hydroxybenzamide. Another, improved method is further described below.

Fumaric acid is commercially available.

The adduct according to the invention may exist in the form of isotopic variants. The invention therefore comprises one or more isotopic variants of the adduct according to the invention, in particular, deuterium-containing adducts.

The term "isotopic variant" is defined as a substance with an unnatural fraction of one or more isotopes from which such a substance is constituted.

The expression "unnatural fraction" is understood to mean a fraction of such an isotope higher than its natural frequency. The natural frequencies of isotopes to be employed in this connection can be found in "Isotopic Compositions of the Elements 1997", Pure Appl. Chem., 70(1), 217-235, 1998.

Examples of such isotopes are stable and radioactive isotopes of hydrogen, carbon, nitrogen, oxygen, phosphorus, sulphur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{125}I$, $^{129}I$ and $^{131}I$.

The adduct according to the invention shows an unforeseeable useful spectrum of pharmacological and pharmacokinetic activity.

It is therefore suitable for use as a medicament for treatment and/or prophylaxis of diseases in humans and animals.

The pharmaceutical efficacy of the adduct according to the invention as IDH1 R132H inhibitor can be explained by the effect of the 3-(2-{[4-(trifluoromethoxy)phenyl]amino}-1-[(1R,5R)-3,3,5-trimethylcyclohexyl]-1H-benzimidazol-5-yl)propanoic acid present.

The present invention further provides for the use of the adduct according to the invention for the treatment and/or prophylaxis of disorders, especially for the treatment of tumours.

The present invention further provides the adduct according to the invention for use in a method for the treatment and/or prophylaxis of tumours.

The present invention further provides for the use of the adduct according to the invention for production of a medicament for the treatment and/or prophylaxis of disorders, especially for the treatment of tumours.

The present invention further provides a process for the treatment and/or prophylaxis of disorders, especially for the treatment of tumours, using a pharmaceutically effective amount of the adduct according to the invention.

Solid tumours that can be treated in accordance with the invention are, for example, tumours of the breast, the respiratory tract, the brain, the reproductive organs, the gastrointestinal tract, the urogenital tract, the eye, the liver, the skin, the head and the neck, the thyroid gland, the parathyroid gland, the bones, and the connective tissue and metastases of these tumours.

Haematological tumours which can be treated are, for example,
multiple myelomas,
lymphomas or
leukaemias.

Breast tumours which can be treated are, for example:
breast carcinomas with positive hormone receptor status
breast carcinomas with negative hormone receptor status
Her-2 positive breast carcinomas
hormone receptor and Her-2 negative breast carcinomas
BRCA-associated breast carcinomas
inflammatory breast carcinomas.

Tumours of the respiratory tract which can be treated are, for example,
non-small-cell bronchial carcinomas such as, for example, squamous cell carcinoma, adenocarcinoma, large-cell carcinoma and
small-cell bronchial carcinomas.

Tumours of the brain which can be treated are, for example,
gliomas,
glioblastomas,
astrocytomas,
meningiomas and
medulloblastomas.

Tumours of the male reproductive organs which can be treated are, for example:
prostate carcinomas,
malignant epididymal tumours
malignant testicular tumours and
penis carcinomas.

Tumours of the female reproductive organs which can be treated are, for example:
endometrial carcinomas
cervix carcinomas
ovarian carcinomas
vaginal carcinomas
vulvar carcinomas Tumours of the gastrointestinal tract which can be treated are, for example:
colorectal carcinomas
anal carcinomas
stomach carcinomas
pancreas carcinomas
oesophagus carcinomas
gall bladder carcinomas
carcinomas of the small intestine
salivary gland carcinomas
neuroendocrine tumours
gastrointestinal stroma tumours Tumours of the urogenital tract which can be treated are, for example:
urinary bladder carcinomas
kidney cell carcinomas carcinomas of the renal pelvis and lower urinary tract
Tumours of the eye which can be treated are, for example:
retinoblastomas
intraocular melanomas
Tumours of the liver which can be treated are, for example:
hepatocellular carcinomas
cholangiocellular carcinomas
Tumours of the skin which can be treated are, for example:
malignant melanomas
basaliomas
spinaliomas
Kaposi sarcomas
Merkel cell carcinomas
Tumours of the head and neck which can be treated are, for example:
larynx carcinomas
carcinomas of the pharynx and the oral cavity
carcinomas of the middle line structures (e.g. NMC, C. A. French, Annu. Rev. Pathol. 2012, 7:247-265)
Sarcomas which can be treated are, for example:
soft tissue sarcomas
osteosarcomas
Lymphomas which can be treated are, for example:
non-Hodgkin lymphomas
Hodgkin lymphomas
cutaneous lymphomas
lymphomas of the central nervous system
AIDS-associated lymphomas
Leukaemias which can be treated are, for example:
acute myeloid leukaemias
chronic myeloid leukaemias
acute lymphatic leukaemias
chronic lymphatic leukaemias
hairy cell leukaemias The adduct according to the invention can act systemically and locally. For this purpose, it can be administered in a suitable manner, for example by the oral, parenteral, pulmonary, nasal, sublingual, lingual, buccal, rectal, dermal, transdermal, conjunctival or otic route, or as implant or stent.

The adduct according to the invention can be administered in administration forms suitable for these administration routes.

Suitable administration forms for oral administration are those which work according to the prior art, which can release the adduct according to the invention rapidly and in a modified manner, for example tablets (uncoated or coated tablets, for example with gastric juice-resistant or retarded-dissolution or insoluble coatings which control the release of the adduct according to the invention), tablets or films/wafers which disintegrate rapidly in the oral cavity, films/lyophilizates, capsules (for example hard or soft gelatin capsules), sugar-coated tablets, granules, pellets, powders, emulsions, suspensions or aerosols.

Parenteral administration can be accomplished with avoidance of a resorption step (for example by an intravenous, intraarterial, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of suspensions, emulsions, lyophilizates or sterile powders.

Suitable administration forms for the other administration routes are, for example, pharmaceutical forms for inhalation (including powder inhalers, nebulizers), nasal drops or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (for example patches), milk, pastes, foams, dusting powders, implants or stents.

The adduct according to the invention can be converted to the administration forms mentioned. This can be accomplished in a manner known per se by mixing with inert, non-toxic, pharmaceutically suitable auxiliaries. These auxiliaries include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colourants (e.g. inorganic pigments, for example iron oxides) and flavour and/or odour correctants.

The present invention furthermore provides medicaments which comprise the adduct according to the invention, typically together with one or more inert, nontoxic, pharmaceutically suitable auxiliaries, and the use thereof for the aforementioned purposes.

The adduct according to the invention is formulated to give pharmaceutical preparations in a manner known per se, by converting the active ingredient(s) to the desired administration form with the auxiliaries customary in the pharmaceutical formulation.

The auxiliaries used may, for example, be carrier substances, fillers, disintegrants, binders, humectants, glidants, absorbents and adsorbents, diluents, cosolvents, emulsifiers, taste correctors, colourants, preservatives, stabilizers, wetting agents, salts for modifying the osmotic pressure or buffers. Reference should be made to Remington's Pharmaceutical Science, 15th ed. Mack Publishing Company, East Pennsylvania (1980).

The pharmaceutical formulations can be present
in solid form, for example as tablets, sugar-coated tablets, pills, suppositories, capsules, transdermal systems or
in semisolid form, for example as ointments, creams, gels, suppositories, emulsions or
in liquid form, for example as tinctures, suspensions or emulsions.

Auxiliaries in the context of the invention may, for example, be salts, saccharides (mono-, di-, tri-, oligo- and/or polysaccharides), proteins, amino acids, peptides, fats, waxes, oils, hydrocarbons and derivatives thereof, and the auxiliaries may be of natural origin or be obtained by synthetic or partially synthetic means.

Useful forms for oral or peroral administration are especially tablets, sugar-coated tablets, capsules, pills, powders, granules, pastilles, suspensions or emulsions.

Useful forms for parenteral administration are especially suspensions or emulsions.

The adduct according to the invention can be used alone or, if required, in combination with one or more other pharmacologically active substances, provided that this combination does not lead to undesirable and unacceptable side effects. The present invention therefore further provides medicaments comprising the adduct according to the invention and one or more further active ingredients, especially for prophylaxis and treatment of the aforementioned disorders.

For example, the adduct according to the invention may be combined with known anti-hyperproliferative, cytostatic or cytotoxic substances which are used for the treatment of neoplastic disorders, but it may also be combined at the same time with those substances having a supporting or constitutive property, combined with those compounds which show positive effects in angiogenesis.

Suitable pharmacologically active substances which are useful for a combination, although not an exhaustive list, include for example:

131I-chTNT, abarelix, abiraterone, aclarubicin, aflibercept, aldesleukin, alemtuzumab, alitretinoin, altretamine, aminoglutethimide, amrubicin, amsacrine, anastrozole, arglabin, arsenic trioxide, asparaginase, axitinib, azacitidine, basiliximab, belotecan, bendamustine, bevacizumab, bexarotene, bicalutamide, bisantrene, bleomycin, bortezomib, bosutinib, brentuximab, buserelin, busulfan, cabazitaxel, cabozantinib-s-malate, calcium folinate, calcium levofolinate, capecitabine, carboplatin, carfilzomib, carmofur, carmustine, catumaxomab, celecoxib, celmoleukin, cediranib, cetuximab, chlorambucil, chlormadinone, chlormethine, cisplatin, cladribine, clodronic acid, clofarabine, copanlisib, crisantaspase, crizotinib, cyclophosphamide, cyproterone, cytarabine, dacarbazine, dactinomycin, darbepoetin alfa, dasatinib, daunorubicin, debrafenib, decitabine, degarelix, denileukin diftitox, denosumab, deslorelin, dexrazoxane hydrochloride, dibrospidium chloride, docetaxel, doxifluridine, doxorubicin, doxorubicin+estrone, eculizumab, edrecolomab, elliptinium acetate, eltrombopag, endostatin, enocitabine, enzalutamide, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glucarpidase, glutoxim, goserelin, histamine dihydrochloride, histrelin, hydroxycarbamide, I-125 seeds, ibandronic acid, ibritumomab tiuxetan, ibrutinib, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, leucovorin, levamisole, lisuride, lobaplatin, lomustine, lonidamine, masoprocol, mechlorethamine, medroxyprogesterone, megestrol, melphalan, mepitiostane, mercaptopurine, mesna, methotrexate, methoxsalen, methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, obinutuzumab, ofatumumab, omacetaxine mepesuccinate, omeprazole, oprelvekin, oxaliplatin, ozogamicin, p53 gene therapy, paclitaxel, palifermin, palladium-103 seed, palonosetron hydrochloride, pamidronic acid, pamidronate disodium, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, pertuzumab, picibanil, pirarubicin, plerixafor, plicamycin, poliglusam, polyestradiol phosphate, polysaccharide-K, pomalidomide, pomatinib, porfimer sodium, pralatrexate, prednimustine, prednisone, procarbazine, quinagolide, radium-223 chloride, raloxifene, raltitrexed, ramucirumab, rasburicase, ranimustine, razoxane, refametinib, regorafenib, risedronic acid, rituximab, romidepsin, romiplostim, roniciclib, ruxolitinib, sargramostim, sipuleucel-T, sizofiran, sobuzoxane, sodium glycididazole, sorafenib, streptozocin, sunitinib, talaporfin, talc, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, I 131 tositumomab, trametinib, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

Generally, the following aims can be pursued with the combination of the adduct according to the invention with other cytostatically or cytotoxically active agents:

improved efficacy in slowing the growth of a tumour, in reducing its size or even in completely eliminating it, compared with treatment with an individual active ingredient;

the possibility of using the chemotherapeutics used in a lower dosage than in the case of monotherapy;

the possibility of a more tolerable therapy with fewer side effects compared with individual administration;

the possibility of treatment of a broader spectrum of neoplastic disorders;

the achievement of a higher rate of response to the therapy;

a longer survival time of the patient compared with present-day standard therapy.

In addition, the adduct according to the invention can also be used in combination with radiotherapy and/or surgical intervention.

Experimental Section

EXAMPLES

Example 1

Preparation of methyl 3-(3-nitro-4-{[(1R,5R)-3,3,5-trimethylcyclohexyl]amino}phenyl)propanoate 402 g (1.77 mol) of methyl 3-(4-fluoro-3-nitrophenyl) propanoate as a solution in 3.0 L of acetonitrile were initially charged with 367 g (2.66 mol) of potassium carbonate and 300 g (2.12 mol) of (1R,5R)-3,3,5-trimethylcyclohexanamine were added. The mixture was stirred for 12 hours under reflux at a jacket temperature of 100° C. After cooling to 20° C., 3.6 L of water were added to the mixture. To improve phase separation, 1.0 L of saturated sodium chloride solution was added. The lower aqueous phase was removed. The organic phases were concentrated under reduced pressure (ca. 50 mbar) at a jacket temperature of 50° C. to give an oily residue.

Yield: 640.5 g (104% of theory) of a highly viscous orange oil.

$^1$H-NMR (400 MHz, DMSO-$d_6$): δ [ppm]=0.75-0.87 (m, 2H), 0.89 (d, 3H), 0.93 (s, 3H), 1.02 (s, 3H), 1.10 (t, 1H), 1.34-1.39 (m, 1H), 1.68-1.83 (m, 2H), 1.99-2.02 (m, 1H), 2.58-2.62 (m, 2H), 2.75-2.79 (m, 2H), 3.57 (s, 3H), 3.73-3.82 (m, 1H), 7.07 (d, 1H), 7.44 (dd, 1H), 7.79 (br. d., 1H), 7.89 (d, 1H).

Example 2

Preparation of methyl 3-(3-amino-4-{[(1R,5R)-3,3,5-trimethylcyclohexyl]amino}phenyl)propanoate dihydrochloride dioxane solvate 640.5 g (1.77 mol) of methyl 3-(3-nitro-4-{[(1R,5R)-3,3,5-trimethylcyclohexyl]amino}phenyl)propanoate (crude product from Example 1) as a solution in 3.2 L of tetrahydrofuran were initially charged with 32 g of palladium catalyst (5% by weight; 0.05 eq., 32 g, 88.5 mmol) in a hydrogenation reactor and the mixture was stirred under a hydrogen atmosphere (1.5 bar positive pressure) at a temperature of 25'C for 10 h. The reaction mixture was filtered off through a pressure filter (Seitz K300 filter plate) and the filtrate was concentrated under reduced pressure (ca. 50 mbar) at a jacket temperature of 50° C. to give an oily residue. The residue was dissolved in 1.3 L of dioxane and to this was added 560 mL of 4N HCl in dioxane (4.4 mol HCl) at an internal temperature of 20° C. over a period of 20 min. In the course of this, the product crystallizes out. This was stirred for 2 h, filtered off and washed twice, each time with 500 mL of MTBE. The moist product was dried in a drying cabinet at a temperature of 40° C. for 4 h under vacuum.

Yield: 785 g (91% of theory, based on use of methyl 3-(4-fluoro-3-nitrophenyl)propanoate) of a pale yellow solid.

$^1$H-NMR (400 MHz, DMSO-$d_6$): δ [ppm]=0.72-0.84 (m, 1H), 0.85-1.05 (m, 10H), 1.19-1.28 (m, 1H), 1.31-1.35 (m, 1H), 1.59-1.71 (m, 2H), 1.90-1.97 (m, 1H), 2.56-2.62 (m, 2H), 2.72-2.78 (m, 2H) 3.51-3.54 (m, 1H), 3.55 (s, 3H), 3.57 (s, 8H, dioxane), 6.28-6.37 (br. m., 5H), 6.69 (br. d., 1H), 6.70 (s, 1H), 7.01 (br. d., 1H).

Example 3

Preparation of 3-(2-{[4-(trifluoromethoxy)phenyl]amino}-1-[(1R,5R)-3,3,5-trimethylcyclohexyl]-1H-benzimidazol-5-yl)propanoic acid To a suspension of 500 g (1.043 mol) of methyl 3-(3-amino-4-{[(1R,5R)-3,3,5-trimethylcyclohexyl]amino}phenyl)propanoate dihydrochloride dioxane solvate in 3.0 L of THF were added 296.5 g (2.29 mol) of N,N-diisopropylethylamine at a temperature of 20° C. and the mixture was stirred for 30 min. 252 g (1.15 mol) of 4-(trifluoromethoxy)phenyl isothiocyanate were added and the temperature maintained at 50° C. for 1 h. Subsequently, 300 g (1.56 mol) of EDC I were added and the mixture was stirred for 4 h under reflux at a jacket temperature of 80° C. The mixture was cooled to 20° C., 1.5 L of 20% aqueous citric acid solution were added, the mixture stirred for 30 min, 1.5 L of MTBE were added and the mixture stirred further for 15 min. The lower aqueous phase was removed. The organic phase was extracted twice, each time with 1.5 L of 4.8% aqueous sodium hydrogen carbonate solution. The organic phase was concentrated under reduced pressure (ca. 50 mbar) at a jacket temperature of 50° C. to give an oily residue to which were subsequently added 3 L of THF and 2 L of 3.7% sodium hydroxide solution (1.56 mol), and the mixture was stirred at a temperature of 50° C. for 3 h. After cooling to 20° C., the mixture was adjusted to a pH of 4 with 10% aqueous hydrochloric acid, 500 mL of saturated sodium chloride solution were added and the aqueous phase was removed. The organic phase was concentrated at a jacket temperature of 80° C. to give an oily residue, to which 4 L of isopropanol were then added and ca. 2.5 L were distilled off at a jacket temperature of 100° C. 900 mL of water were added at the same time over a period of 20 min at an internal temperature of 80° C. In the course of this, the product crystallized out from the hot mixture. After cooling to 20° C., the product was filtered off and washed successively with 500 mL of isopropanol and 500 mL of water. The moist product was dried in a drying cabinet at a temperature of 60° C. for 16 h under vacuum.

Yield: 398 g (77% of theory) of a white crystalline solid (m.p.: 248° C.).

$^1$H-NMR (400 MHz, DMSO-$d_6$): δ [ppm]=0.93 (s, 3H), 0.96 (s, 3H), 1.03 (s, 3H), 1.04-1.12 (m, 1H), 1.35-1.44 (m, 2H), 1.70-1.92 (m, 3H), 2.03 (t, 1H), 2.43-2.60 (m, 2H), 2.85 (t, 2H), 4.63 (t, 1H), 6.90 (d, 1H), 7.24 (s, 1H), 7.32 (d, 2H), 7.42 (d, 1H), 7.79 (d, 2H), 8.98 (br. s., 1H), 12.06 (br. s., 1H).

Example 4

Preparation of the adduct (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4)

To 296 g (603 mmol) of 3-(2-{[4-(trifluoromethoxy)phenyl]amino}-1-[(1R,5R)-3,3,5-trimethylcyclohexyl]-1H-benzimidazol-5-yl)propanoic acid and 35 g (301.5 mmol) of fumaric acid were added 4.5 L of isopropanol and the mixture was heated at reflux temperature with stirring. The solution, temperature-controlled at 80° C., was filtered and subsequently 3.25 L of isopropanol were distilled off during which the product crystallized out. After cooling to 20° C., the product was filtered off and washed with 500 mL of isopropanol. The moist product was dried in a drying cabinet at a temperature of 60° C. for 16 h under vacuum.

Yield: 280 g (89% of theory) of a white crystalline solid (m.p.: 235° C.).

$^1$H-NMR (400 MHz, DMSO-$d_6$): δ [ppm]=0.93 (s, 3H), 0.96 (s, 3H), 1.03 (s, 3H), 1.04-1.12 (m, 1H), 1.35-1.44 (m, 2H), 1.70-1.92 (m, 3H), 2.03 (t, 1H), 2.43-2.60 (m, 2H), 2.85 (t, 2H), 4.63 (t, 1H), 6.62 (s, 2H; fumaric acid), 6.90 (d, 1H), 7.24 (s, 1H), 7.32 (d, 2H), 7.42 (d, 1H), 7.79 (d, 2H), 8.98 (br. s., 1H), 12.1-12.6 (br. m., 1H+fumaric acid).

Oral Bioavailability

Compound A is pure 3-(2-{[4-(trifluoromethoxy)phenyl]amino}-1-[(1R,5R)-3,3,5-trimethylcyclohexyl]-1H-benzimidazol-5-yl)propanoic acid in crystalline form, as obtained in a method according to Example 3.

Compound B is the adduct according to the invention, (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid in crystalline form, as obtained in a method according to Example 4.

The relative bioavailability was determined by studies in Wistar rats.

Compound A was firstly administered orally in the form of a solution. For this purpose, the active ingredient was dissolved in a mixture of 80% polyethylene glycol having an average molecular weight of 400 (PEG400) and 20% water. The active ingredient solution is the reference point for determining the relative bioavailability (formulation A1).

Compound A was also administered orally in the form of a tylose suspension (formulation A2).

Compound B was likewise administered orally in the form of a tylose suspension (formulation B).

Tylose (Tylose® MH 300 (Sigma)) is a methyl hydroxyethyl cellulose ether, which is used in materials as a water-soluble non-ionic polymer, in order to achieve water retention, binding, thickening, film formation and colloidal properties.

To prepare a 0.5% aqueous tylose suspension (w/v), tylose was stirred and swelled for about 12 hours in pure water, whereupon a viscous mixture was formed. Compound A and compound B were each ground into the viscous mixture, whereupon the corresponding tylose suspensions were formed (formulation A2 and formulation B).

Figure 1B:
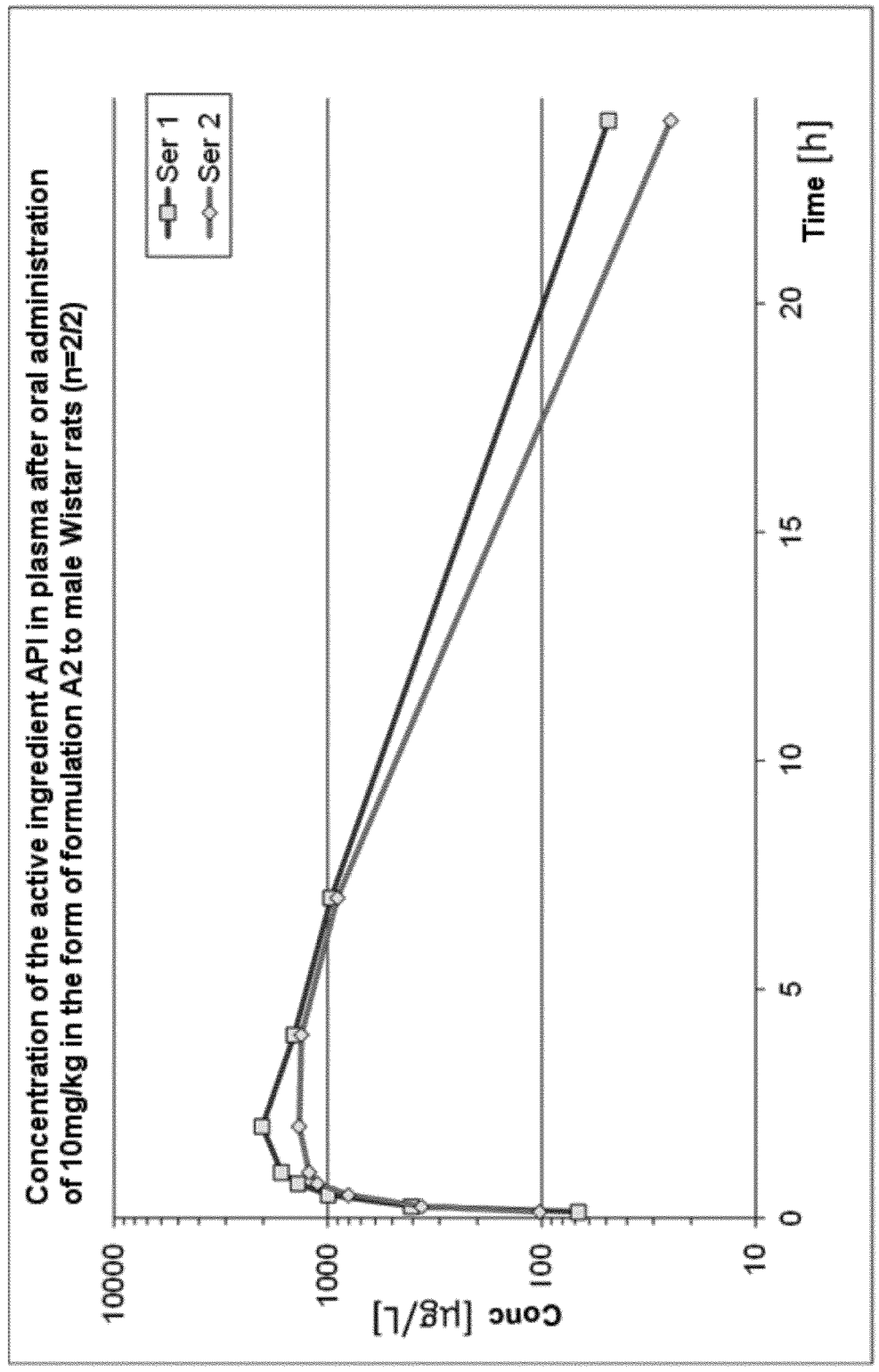
Figure 1C:
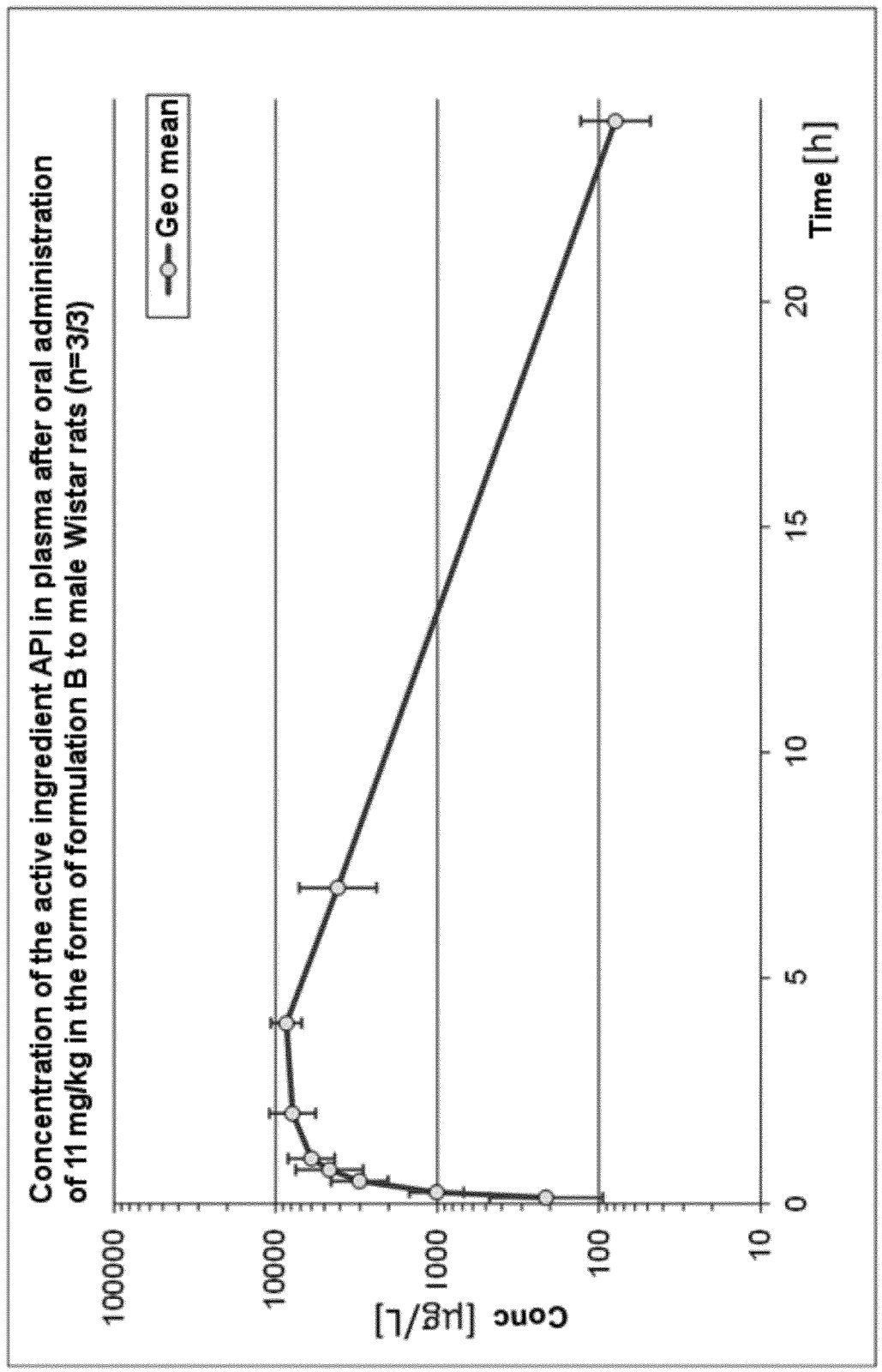

FIGS. 1a, 1b and 1c show the plasma concentrations of the active ingredient 3-(2-{[4-(trifluoromethoxy)phenyl]amino}-1-[(1R,5R)-3,3,5-trimethylcyclohexyl]-1H-benzimidazol-5-yl)propanoic acid (active ingredient API) after oral administration of compound A in the form of a solution (formulation A1, FIG. 1a), after oral administration of compound A in the form of a suspension (formulation A2, FIG. 1b) and after oral administration of compound B in the form of a suspension (formulation B, FIG. 1c).

For formulation A1, 5 mL/kg body weight were administered. This corresponded to an amount of active ingredient API of 10 mg/kg.

For formulation A2, 5 mL/kg body weight were administered. This corresponded to an amount of active ingredient API of 10 mg/kg.

For formulation B, 2 mL/kg body weight were administered. This corresponded to an amount of active ingredient API of 10.6 mg/kg.

Plasma concentrations were determined by collecting about 0.4 mL of blood in each case via an indwelling venous catheter. The blood samples were centrifuged (about 5 minutes) in order to obtain the plasma. The plasma samples were analyzed by LC/MS/MS with respect to the active ingredient 3-(2-{[4-(trifluoromethoxy)phenyl]amino}-1-[(1R,5R)-3,3,5-trimethylcyclohexyl]-1H-benzimidazol-5-yl)propanoic acid.

Pure 3-(2-{[4-(trifluoromethoxy)phenyl]amino}-1-[(1R,5R)-3,3,5-trimethylcyclohexyl]-1H-benzimidazol-5-yl)propanoic acid showed a bioavailability of 25% in the $F_{Rel}$ experiment.

For the 4:1 adduct with fumaric acid, a bioavailability of 110% was determined in the $F_{Rel}$ experiment.

Therefore, the adduct according to the invention shows distinctly higher bioavailability than pure 3-(2-{[4-(trifluoromethoxy)phenyl]amino}-1-[(1R,5R)-3,3,5-trimethylcyclohexyl]-1H-benzimidazol-5-yl)propanoic acid.

X-Ray Powder Diffractogram

FIG. 2 shows the X-ray powder diffractogram of the adduct according to the invention in crystalline form, as obtained in a method according to Example 4.

An automated STOE powder diffractometer was used in transmission mode using germanium-monochromatized CuK$\alpha_1$ radiation. The X-ray tube with copper anode was operated at 40 kV and 40 mA. The 2Θ scans were recorded between 2°≤2Θ≤40° (step size 0.5°). The software STOE WinX$^{pow}$ was used to evaluate the data.

The maxima of the 2Θ values are listed in Table 1.

TABLE 1

| XRPD reflection table Band maxima [2 theta] |
|---|
| 5.4 |
| 6.8 |
| 7.4 |
| 8.7 |
| 8.9 |
| 10.2 |
| 10.3 |
| 10.8 |
| 11.1 |
| 11.6 |
| 12.4 |
| 12.7 |
| 13.5 |

TABLE 1-continued

| XRPD reflection table Band maxima [2 theta] |
|---|
| 14.0 |
| 14.3 |
| 14.6 |
| 14.9 |
| 15.3 |
| 15.5 |
| 15.9 |
| 16.2 |
| 16.8 |
| 17.0 |
| 17.3 |
| 17.6 |
| 17.9 |
| 18.6 |
| 18.7 |
| 19.2 |
| 19.4 |
| 19.7 |
| 20.0 |
| 20.4 |
| 20.9 |
| 21.1 |
| 21.3 |
| 21.6 |
| 22.3 |
| 22.8 |
| 22.9 |
| 23.0 |
| 23.6 |
| 24.2 |
| 24.4 |
| 24.9 |
| 25.0 |
| 25.4 |
| 26.0 |
| 26.5 |
| 26.9 |
| 27.1 |
| 27.4 |
| 27.7 |
| 28.0 |
| 28.2 |
| 28.8 |
| 29.4 |
| 29.6 |
| 31.0 |
| 31.6 |
| 32.5 |
| 33.1 |
| 33.7 |
| 34.0 |
| 34.5 |
| 34.7 |
| 35.0 |
| 36.1 |
| 36.5 |
| 36.9 |
| 37.7 |

FIG. 3 shows the Raman spectrum of the adduct according to the invention in crystalline form, as obtained in a method according to Example 4. The positions of the band maxima are listed in Table 2.

TABLE 2

| Raman spectrum band table Raman bands [cm$^{-1}$] |
|---|
| 3088 |
| 3047 |
| 2934 |
| 2910 |
| 2874 |
| 2771 |

TABLE 2-continued

Raman spectrum band table
Raman bands [cm$^{-1}$]

2717
1658
1632
1615
1521
1463
1451
1420
1338
1306
1294
1277
1245
1198
1184
1167
1155
1127
1109
1077
1049
1018
979
961
943
922
908
877
866
839
817
789
767
714
700
685
646
631
613
568
517
503
450
438
416
388
358
339
330
102

Inhibition of IDH1 R132H in a Biochemical Assay

IDH1 R132H catalyzes the NADPH-dependent reduction of alpha-ketoglutarate (α-KG) to (2R)-2-hydroxyglutarate (2-HG). NADPH consumption is determined by luminescence.

The biochemical reactions were carried out at 32° C. in a 384-well titre plate in a reaction volume of 41 µL in each case and under the following buffer conditions: 50 mM Tris pH 7.5, 100 mM NaCl, 20 mM MgCl$_2$, 0.05% BSA, 0.01% Brij, 1 µM NADPH, and 250 µM α-KG. The IDH1 R132H enzyme was used at a final concentration of 1.5 nM. Test compounds were assayed in a concentration range of 0.002 to 10 µM. The final DMSO concentration was 2.4%.

The reaction was incubated for 30 minutes, after which 40 µL of a detection mixture (0.75 µg/ml luciferase, 0.02 U/ml oxidoreductase, 4 µg/mL FMN, 2 µL/ml decanal/ethanol, 50 mM Tris pH 7.5, 0.5% glycerol, 0.01% Tween 20, 0.05% BSA) were added. The luminescence was determined using a luminescence reader (10 seconds measurement time, 1 second integration period, 30% sensitivity). The drop in luminescence is proportional to the activity of mIDH1. IC$_{50}$ values were determined by interpolation from plots of the relative luminescence against the inhibitor concentration. The result is summarized in Table 3.

TABLE 3

IC$_{50}$ in the biochemical IDH1 R132H assay

| Test compound | IDH1 R132H IC$_{50}$ [µM] |
|---|---|
| 3-(2-{[4-(trifluoromethoxy)phenyl]amino}-1-[(1R,5R)-3,3,5-trimethylcyclohexyl]-1H-benzimidazol-5-yl)propanoic acid | 0.02 |

Inhibition of IDH1 R132H in a Cellular Assay

Concentrations of (2R)-2-hydroxyglutarate (2HG) were determined in a medium of a cell line having an overexpession of the mutated isocitrate dehydrogenase protein. mIDH catalyzes the NADPH-dependent reduction of alpha-ketoglutarate to 2-HG. Cells (LN229 R132H, Mohrenz et al., Apoptosis (2013) 18:1416-1425) were cultured in DMEM containing 10% FCS. The cells were obtained using trypsin and placed in 96-well titre plates. The cells were incubated overnight at 37° C. in 5% $CO_2$. On the next day, test compounds were added to the cells. The final concentration of DMSO was 0.1% and DMSO controls were used. The titre plates were then placed in an incubator for 24 hours.

2-HG was measured using the method published by Balss et al. (Acta Neuropathol (2012) 124: 883-891). $HClO_4$ was added to each well and the titre plates were centrifuged. Aliquots were removed and incubated with hydroxyglutarate dehydrogenase (HGDH), diaphorase, NAD+ and resazurin. The conversion of resazurin to resorufin was determined by fluorescence spectroscopy at Ex 540 nm Em 600 nm. The increase in the fluorescence signal is proportional to formation of 2-HG. $IC_{50}$ values were determined by interpolation from plots of the relative fluorescence against the inhibitor concentration. The result is summarized in Table 4.

TABLE 4

| Test compound | IDH1 R132H $IC_{50}$ [μM] |
|---|---|
| $IC_{50}$ in the cellular IDH1 R132H assay | |
| 3-(2-{[4-(trifluoromethoxy)phenyl]amino}-1-[(1R,5R)-3,3,5-trimethylcyclohexyl]-1H-benzimidazol-5-yl)propanoic acid | 0.08 |

The invention claimed is:

1. An adduct which is (2E)-But-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4).

2. The adduct according to claim 1 in crystalline form, characterized by maxima in the X-ray diffractogram at the following 2 theta angles: 5.4, 6.8, 10.2, 10.3, 10.8, 11.1, 16.8, and 21.6.

3. The adduct according to claim 1 in crystalline form, characterized by maxima in the Raman spectrum at the following wavenumbers in units of $cm^{-1}$:

3088, 3047, 2934, 2910, 2874, 2771, 2717, 1658, 1632, 1615, 1521, 1463, 1451, 1420, 1338, 1306, 1294, 1277, 1245, 1198, 1184, 1167, 1155, 1127, 1109, 1077, 1049, 1018, 979, 961, 943, 922, 908, 877, 866, 839, 817, 789, 767, 714, 700, 685, 646, 631, 613, 568, 517, 503, 450, 438, 416, 388, 358, 339, 330, and 102.

4. A method for preparing the adduct according to claim 1, comprising the steps of:

introducing 3-(2-{[4-(trifluoromethoxy)phenyl]amino}-1-[(1R,5R)-3,3,5-trimethylcyclohexyl]-1H-benzimidazol-5-yl)propanoic acid and (2E)-but-2-enedioic acid in isopropanol, wherein for 1 mol of 3-(2-{[4-(trifluoromethoxy)phenyl]amino}-1-[(1R,5R)-3,3,5-trimethylcyclohexyl]-1H-benzimidazol-5-yl)propanoic acid, 0.3 to 0.8 mol of (2E)-but-2-enedioic acid are used;

heating the resulting mixture with stirring up to the boiling point to obtain a clear solution; and crystallizing out of the adduct (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4).

5. A method for treatment or prophylaxis of a tumour, comprising administering to a patient in need thereof a therapeutically effective amount of the adduct of claim 1.

6. A pharmaceutical composition comprising the adduct according to claim 1.

7. The pharmaceutical composition according to claim 6, comprising one or more additional active ingredients.

8. The pharmaceutical composition according to claim 6, comprising one or more inert, non-toxic, pharmaceutically acceptable auxiliaries.

9. A method for treatment of a tumour, comprising administering to a patient in need thereof the pharmaceutical composition of claim 6.

10. The method of claim 4, wherein the step of crystallizing out of (2E)-but-2-enedioic acid-3-(2-{[4-(trifluoromethoxy)phenyl]amino}-1-[(1R,5R)-3,3,5-trimethylcyclohexyl]-1H-benzimidazol-5-yl)propanoic acid (1:4) comprises concentrating the solution.

11. The method of claim 5, wherein the method is for treatment of a tumour.

* * * * *